US008658948B2

(12) United States Patent
Charles

(10) Patent No.: US 8,658,948 B2
(45) Date of Patent: Feb. 25, 2014

(54) DOCKING STATION WITH TEMPERATURE CONTROL AND ELECTRONIC IDENTIFICATION SYSTEM

(75) Inventor: Steven T. Charles, Memphis, TN (US)

(73) Assignee: Alcon Research, Ltd., Fort Worth, TX (US)

(*) Notice: Subject to any disclaimer, the term of this patent is extended or adjusted under 35 U.S.C. 154(b) by 514 days.

(21) Appl. No.: 12/640,427

(22) Filed: Dec. 17, 2009

(65) Prior Publication Data

US 2011/0152844 A1 Jun. 23, 2011

(51) Int. Cl.
*H05B 1/02* (2006.01)
(52) U.S. Cl.
USPC ........... 219/518; 219/506; 219/385; 219/521; 312/209; 312/236; 604/113; 604/114
(58) Field of Classification Search
USPC ......... 219/385, 386, 395, 401, 413, 406, 432, 219/433; 432/18, 32, 34, 51, 52, 55; 122/379; 604/114, 291
See application file for complete search history.

(56) References Cited

U.S. PATENT DOCUMENTS

| 4,287,408 | A | * | 9/1981 | Wilson | 219/475 |
|---|---|---|---|---|---|
| 4,906,816 | A | * | 3/1990 | van Leerdam | 392/470 |
| 4,910,386 | A | * | 3/1990 | Johnson | 219/385 |
| 5,164,161 | A | | 11/1992 | Feathers et al. | |
| 5,399,007 | A | * | 3/1995 | Marconet | 312/209 |
| 5,862,672 | A | | 1/1999 | Faries, Jr. et al. | |
| 6,259,067 | B1 | * | 7/2001 | Faries et al. | 219/428 |
| 2003/0024919 | A1 | * | 2/2003 | Julius | 219/385 |
| 2003/0085215 | A1 | | 5/2003 | Rix | |
| 2006/0046226 | A1 | | 3/2006 | Bergler et al. | |
| 2006/0213205 | A1 | | 9/2006 | Reverendo | |
| 2007/0000910 | A1 | * | 1/2007 | Faries et al. | 219/506 |
| 2007/0015975 | A1 | * | 1/2007 | Faries et al. | 600/300 |

FOREIGN PATENT DOCUMENTS

WO WO 2005/067806 7/2005

OTHER PUBLICATIONS

International Search Report for PCT/US2010/057032, 2 pages.
Written Opinion of the international Searching Authority, International Application No. PCT/US2010/057032, Feb. 2, 2011, 6 pages.

* cited by examiner

*Primary Examiner* — Gene Kim
*Assistant Examiner* — John E Simms, Jr.
(74) *Attorney, Agent, or Firm* — W. David Lee

(57) ABSTRACT

Disclosed is an exemplary surgical system employing a temperature controlled docking station. The surgical system may include an articulating arm that is selectively moveable within a range of positions. A tray for receiving items used in performing a procedure may be attached to the articulating arm. The docking station may be attached to the tray. The docking station may include a heating element for selectively heating the docking station, a temperature sensor for monitoring a temperature of the docking station, and a reader configured for collecting information associated with an article placed in the docking station. The surgical system may also include a controller operably connected to the heating element, the temperature sensor, and the reader. The controller may be configured to adjust a heat output of the heating element in response to a signal received from the temperature sensor and/or the reader.

3 Claims, 5 Drawing Sheets

US 8,658,948 B2

DOCKING STATION WITH TEMPERATURE CONTROL AND ELECTRONIC IDENTIFICATION SYSTEM

BACKGROUND

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When trauma or disease causes the lens to become less transparent, vision deteriorates due to the diminished light that is transmitted to the retina. This deficiency in the lens of the eye is medically known as a cataract. An accepted treatment for this condition is surgical removal of the lens and replacement of the lens function by an artificial intraocular lens (IOL).

One accepted method for treating cataractous lenses is to remove the lens by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by the IOL.

The IOL is generally implanted using an insertion apparatus or device, such as an intraocular injection cartridge, that rolls, folds, or otherwise configures the lens for delivery through the small opening in the eye in a way that reduces trauma and expedites post-surgery healing. Injectors for delivering IOLs typically employ a handpiece and a cartridge having a hollow insertion tube or cannula through which the folded IOL is passed using a pushrod. The cartridges may be made of disposable materials, such as plastics, and remain in a sterile package until ready for coupling with the handpiece. Some injectors operate without the cartridge and are reusable. The IOL may be stored separately and transferred to a load chamber in the injector or cartridge just prior to delivery. Typically, the load chamber is first partially filled with a liquid or gel, for example, a viscoelastic medium or ophthalmic viscosurgical device (OVD). The lubricating viscoelastic facilitates passage of the IOL through the injector. The viscoelastic substances may be preloaded in a syringe, typically having a thin cannula tip through which the viscoelastic is delivered to the load chamber in the IOL injector.

The IOL is placed in the IOL injector in a folded state. The IOL is injected into the eye through the same small incision used to remove the diseased lens. The tip of the IOL injector is inserted into the incision, and the lens is delivered into the eye.

IOLs may be manufactured from a variety of materials, and include polymers that exhibit specific characteristics. These characteristics allow the lens to be folded, and when delivered into the eye, allow the lens to unfold into the proper shape. The polymers used to make these lenses have characteristics that tend to be temperature dependant. Heating the polymer allows the IOL to be compressed and folded more easily, thus allowing it to fit through a smaller incision. A smaller incision is desirable because it promotes faster healing and is less traumatic for the patient.

The temperature characteristics of the polymers used to make IOLs may have a significant impact on the lens implantation process. For some polymers, a change in hardness or viscosity occurs over a relatively narrow temperature range. For example, at colder temperatures, the polymer may become brittle and break if folded. At higher temperatures, the polymer may become gummy and lose its shape retaining ability. Therefore, it may be advantageous to maintain the polymer in a specific temperature range to enable the IOL to maintain its physical integrity.

In practice, some surgeons have resorted to manually heating IOLs, for example, using the outside of autoclaves or warmers designed to warm baby wipes. Such warming, however, is uncontrolled and unlikely to warm the IOL to an optimum temperature. As previously noted, the polymers used to manufacture artificial lenses are sensitive to temperature, and more precise temperature control may help achieve desired results.

DETAILED DESCRIPTION

Figure 1:
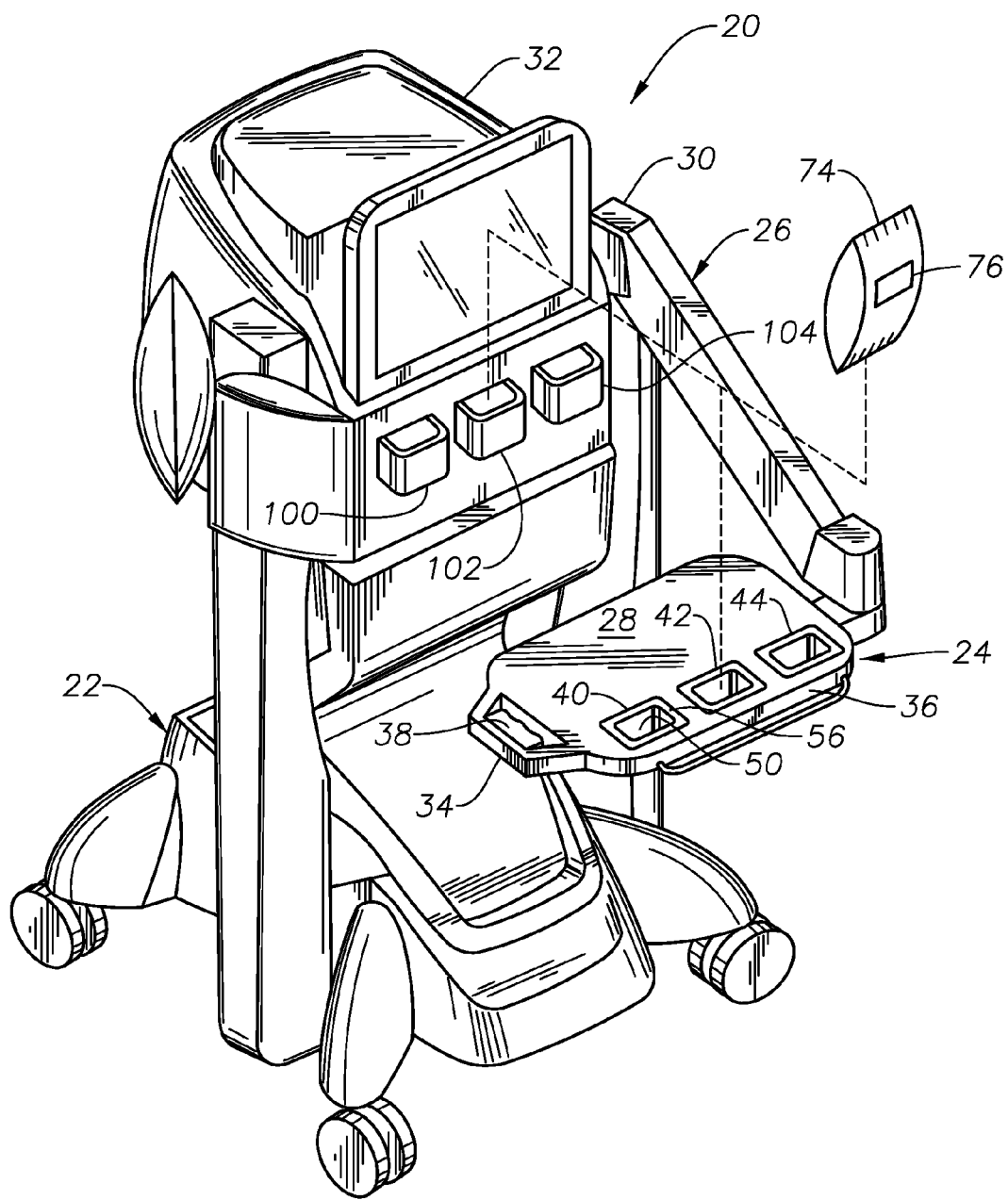
FIG. 1 is a front perspective view of an exemplary ophthalmic surgical console employing a temperature controlled docking station.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Figure 2:
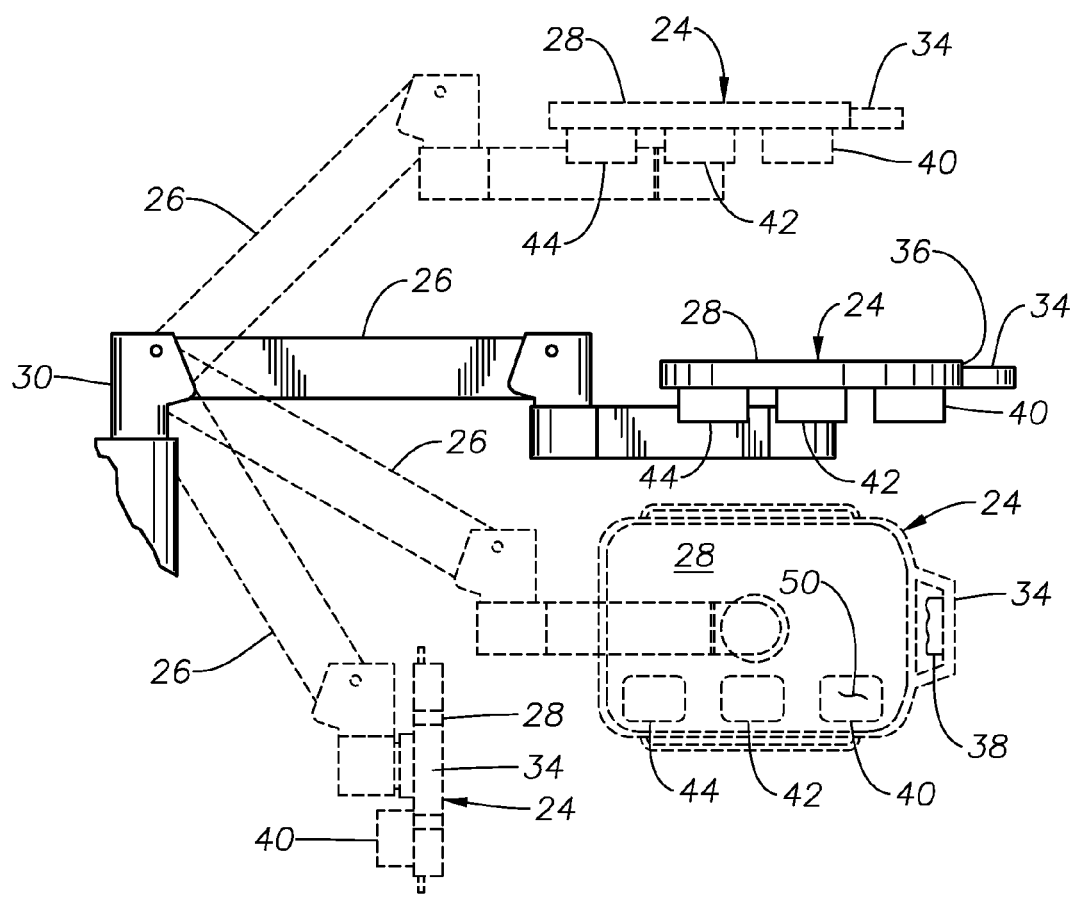
FIG. 2 is a plan view of the docking station shown attached to a tray assembly of the surgical console, the tray shown in a range of exemplary positions.

Referring to FIGS. 1 and 2, an exemplary ophthalmic surgical console 20 for performing various ophthalmic procedures, such as phacoemulsification for removing a diseased eye lenses, is illustrated. Surgical console 20 includes an optional integral cart 22 for enabling the console to be conveniently moved from one location to another. Surgical console 20 may include a tray 24 attached to an articulating support arm 26. Tray 24 may include a tray surface 28 for temporary storage of various instruments, equipment, devices, handpieces, and consumables during a surgical procedure. An end 30 of support arm 26 may be moveably connected to a housing 32 of the console. Support arm 26 may include various joint assemblies that enable the tray to be selectively moved within a desired range of adjustable height and positions, as shown in FIG. 2, to facilitate a broad array of procedures. Tray 24 may include a tray positioning handle 34 extending outward from a circumferential edge 36 of the tray. A release handle 38 for unlocking tray support arm 26 is arranged within tray positioning handle 34 for easy access.

Tray 24 may include one or more temperature controlled docking stations 40, 42 and 44. The docking stations provide convenient and readily accessible receptacles for temporarily storing various components of an intraocular lens injection system, for example, an injection cartridge, an injection handpiece, an intraocular lens (IOL), and a syringe for apply a viscoelastic material to the injection cartridge prior to injecting the IOL into the eye cavity. The docking stations may also be selectively operated to warm the injection system components within a selected range of temperatures to optimize performance of the lens injection system.

Docking stations 40, 42 and 44 may employ various configurations to suit a particular application. For the sake of discussion, each of the docking stations 40, 42 and 44 is shown to have the same general configuration. In practice, each docking station may have the same or a different configuration than either of the remaining docking stations. Since each of the docking stations 40, 42 and 44 is illustrated as having the same general configuration, the docking stations will be described with reference to docking station 40, but the description shall also be applicable to the remaining two docking stations 42 and 44.

Figure 3:
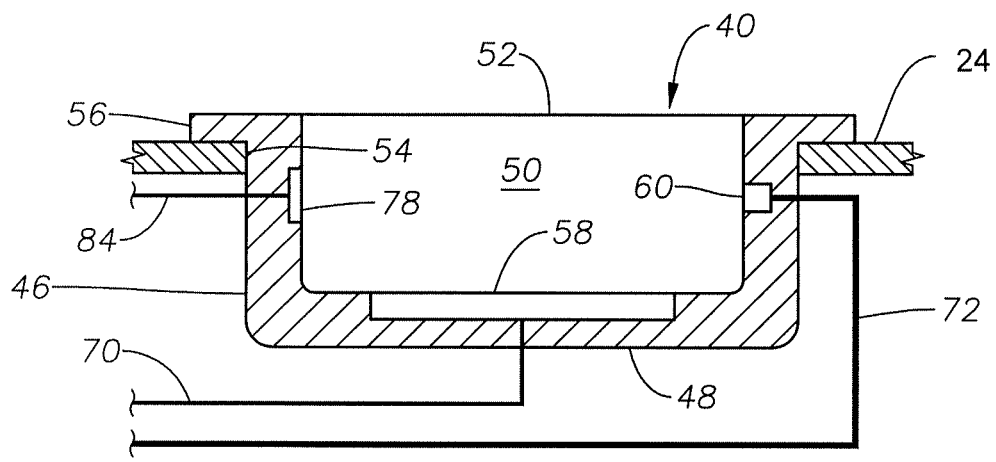
FIG. 3 is a partial cross sectional view of a portion of the docking station and tray assembly of FIG. 1.

With reference to FIGS. 1-3, docking station 40 may have a generally cup-like concave configuration that includes a side wall 46 and an end wall 48 attached thereto. Side wall 46 and end wall 48 at least partially define an interior cavity 50 for receiving the various components of the intraocular lens injection system. The interior cavity 50 may be shaped to generally conform to the shape of particular components, such as an OVD syringe or a lens cartridge, so that the correct docking station 40 can be easily identified for each component. The injection system components are received through a generally open end 52 located opposite end wall 48. Docking station 40 may be attached to tray 24 by arranging the docking station within an aperture 54 that extends through tray 24. Docking station 40 may include a flange 56 that engages a portion of tray 24 for positioning the docking station within aperture 54. In the illustrated exemplary configuration, gravity may be relied upon to hold the docking station in place relative to tray 24. More permanent attaching arrangements may also be employed for connecting docking station 40 to tray 24, such as adhesive, screws, rivets, clips, and depending on the material composition of tray 24 and docking station 40, brazing, soldering and welding.

Continuing to refer to FIG. 3, docking station 40 may also include a heating element 58 for selectively heating side wall 46 and bottom wall 48 of docking station 40. To help uniformly distribute the heat throughout docking station 40, side wall 46 and bottom wall 48 may be constructed from a material having a relatively high thermally conductivity. A temperature sensor 60 may be employed for monitoring a temperature of docking station 40.

Figure 4:
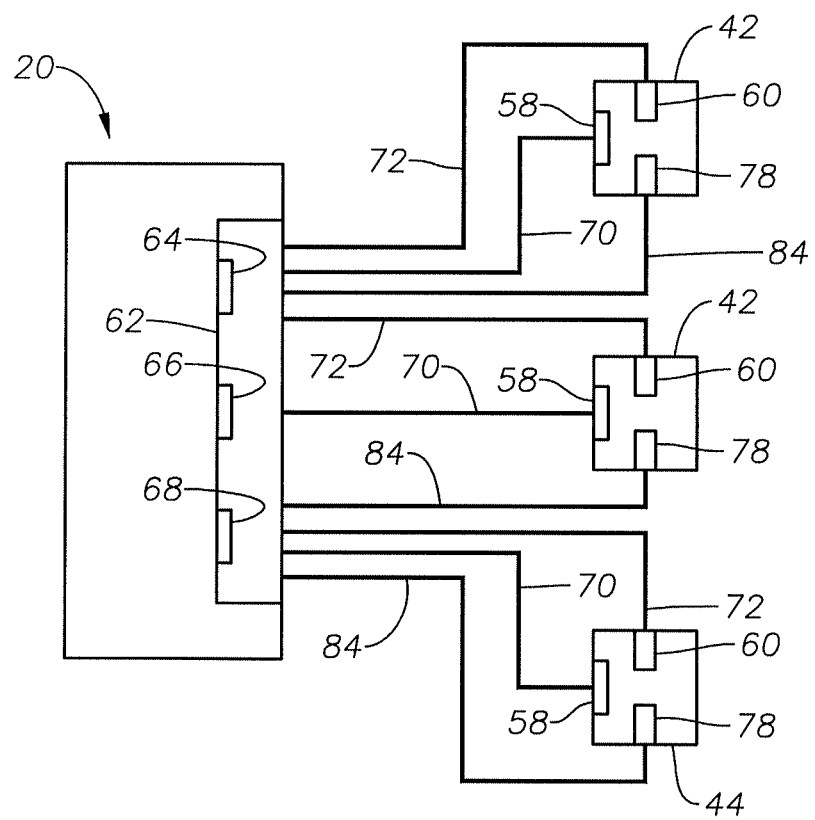
FIG. 4 is a schematic diagram of the exemplary ophthalmic surgical console shown in FIG. 1.

Referring to FIG. 4, surgical console 20 may include a central processing unit (CPU) 62. CPU 62 may include one or more memories 64 for storing, and one or more processors 66 for executing instructions, such as those included in a computer program. Each processor 66 may employ any of a number of computer operating systems known to those skilled in the art, including, but by no means limited to, known versions and/or varieties of the Microsoft Windows® operating system, the Unix operating system (e.g., the Solaris® operating system distributed by Sun Microsystems of Menlo Park, Calif.), the AIX UNIX operating system distributed by International Business Machines of Armonk, New York, and the Linux operating system. Computer-executable instructions may be compiled or interpreted from computer programs created using a variety of programming languages and/or technologies known to those skilled in the art, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of known computer-readable media.

Surgical console 20 may also include a computer-readable medium 68 that may include any tangible medium that participates in providing data (e.g., instructions), which may be read by a computer. Such a medium may take many forms, including, but not limited to, non-volatile media and volatile media. Non-volatile media include, for example, optical or magnetic disks and other persistent memory. Volatile media include dynamic random access memory (DRAM), which typically constitutes a main memory. Such instructions may be transmitted by one or more transmission media, including coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave, or any other medium from which a computer can read.

Surgical console 20 may also include various databases or data stores that may include various kinds of mechanisms for storing, accessing, and retrieving various kinds of data, including a hierarchical database, a set of files in a file system, an application database in a proprietary format, a relational database management system (RDBMS), etc. Each such database or data store is generally included within a computing device employing a computer operating system such as one of those mentioned above, and are accessed via a network in any one or more of a variety of manners, as is known. A file system may be accessible from a computer operating system, and may include files stored in various formats. An RDBMS generally employs the known Structured Query Language (SQL) in addition to a language for creating, storing, editing, and executing stored procedures, such as the PL/SQL language mentioned above.

With continued reference to FIG. 4, an operating temperature of docking station 40 may be selectively controlled by adjusting a heat output of heating element 58. For example, heating element 58 may be operably connected to CPU 62 through connector 70. Temperature sensor 60 used to monitor the temperature of docking station 40 may also be operably connected to CPU 62 through a connector 72. The temperature sensor may send a signal to CPU 62 indicative of the temperature of docking station 40. In response to the signal received from temperature sensor 60, CPU 62 may adjust the power input to heating element 58 to control its heat output, and thus the temperature of docking station 40.

Continuing to refer to FIG. 4, docking stations 40, 42 and 44 may each include a separate heating element 58 and temperature sensor 60 to enable individualized temperature control of each docking station. Each heating element 58 and temperature sensor 60 may be operably connected to a single shared processor 66 (as shown in FIG. 4), or the heating element 58 and temperature sensor 60 of each individual docking station may be operably connected to their own separate processor 66. Each processor 66 may be configured to selectively control the heat output of each heating element 58 associated with each of the respective docking stations 40, 42 and 44.

Referring again to FIG. 1, the various components of the intraocular injection system may be enclosed in a pack 74 for protecting the sterility of the components prior to use. Pack 74 may include a single component, such as an OVD, or a combination of components. Pack 74 may include an identification device 76, such as an external bar code, that identifies the contents of pack 74. Identification device 76 may also employ other types of automatic identification and data capture technologies, for example, Radio Frequency Identification (RFID), magnetic stripes, and Optical Character Recognition (OCR), to name a few. Identification device 76 may be arranged external to pack 74, such as with a bar code or optical device, or internal, such as with a RFID or magnetic device. Identification device 76 may be encoded with data identifying the components contained within pack 74, as well as other information. Referring also to FIGS. 3 and 4, docking station 40 may include a reader 78 capable of capturing the data stored on identification device 76. Depending on the technology employed, reader 78 may be a bar code reader, a CCD camera, a CMOS sensor, a radio frequency sensor, a magnetic field sensor, or other suitable sensor. Reader 78 may be operably connected to CPU 62 through a connector 80. When pack 74 is placed in docking station 40, reader 78 senses identification device 76 and proceeds to collect the data stored on identification device 76 and transmits the data to CPU 62. CPU 62 may use the data, under appropriate software control, to automatically adjust the operating temperature of docking station 40 to coincide with the components contained within pack 76 using factory or user programmable settings. The collected data may also be used for a variety of other purposes, for example, optimizing temperature control of a specific IOL and specific OVD placed in the docking station; confirming that the IOL in the docking station corresponds with the IOL selected for the specific patient; optimizing an IOL-OVD match to minimize friction between the IOL and a corresponding injector cartridge; determining optimum injector velocity and force parameters when using a power injector; as input for inventory control and/or billing functions; and as input for electronic medical records. Identification device 76 and reader 78 may be any of a variety of suitable electrical, magnetic and optical devices.

In addition to managing the temperature of the components, CPU 62 may also use the data regarding the components for various functions pertaining to patient management and control of surgical procedures. For example, CPU 62 may verify that the components match patient data describing a surgical procedure to be performed on the patient. In another example, CPU 62 may verify the compatibility of the components with an injection system for the IOL, such as confirming that a cartridge is compatible with an injection handpiece selected for the surgical procedure.

Figure 5:
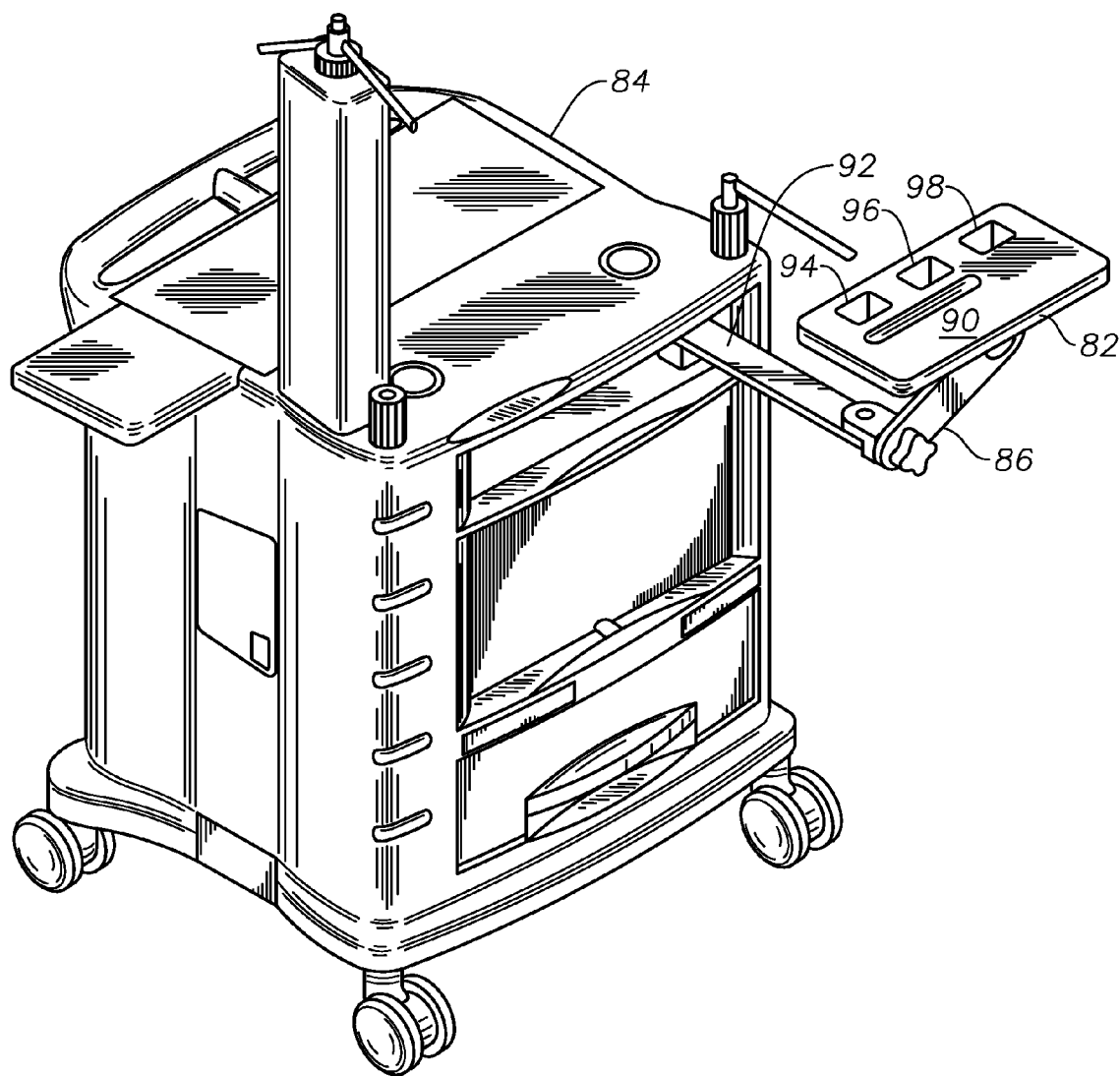
FIG. 5 is a front perspective view of an exemplary cart for supporting a surgical console, with the docking station shown attached to a tray connected to the cart.
Figure 6:
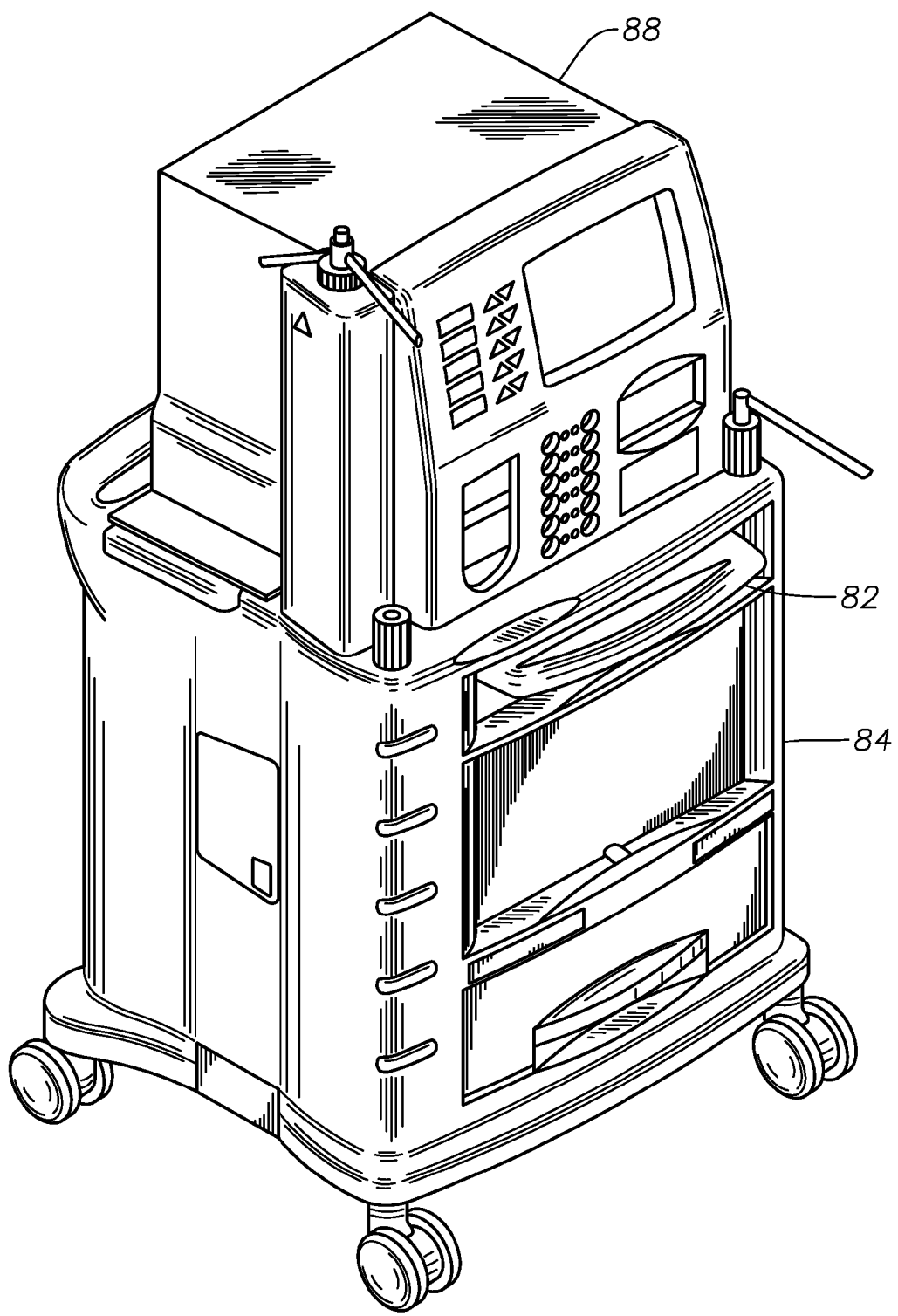
FIG. 6 is a front perspective view of the exemplary cart shown in FIG. 5, with an ophthalmic surgical console attached to the cart.

In FIG. 1, tray 24 with integrated docking stations 40, 42 and 44, and articulating support arm 26, are shown connected to surgical console 20 that also includes integrated cart 22. The tray and arm assembly may also be attached to a cart that is not configured as an integral part of the surgical console. As shown in FIGS. 5 and 6, a tray 82 may be attached to a surgical cart 84 by way of articulating support arm 86. Surgical cart 84 may be configured to support a surgical console 88, as shown in FIG. 6. Tray 82 may include a tray surface 90 for temporary storage of various instruments, equipment, devices, handpieces, and consumables during a surgical procedure. An end 92 of support arm 86 may be moveably connected to surgical cart 84. Support arm 86 may include various joint assemblies that enable the tray to be selectively moved within a desired range of adjustable height and positions.

Tray 82 may include one or more temperature controlled docking stations 94, 96 and 98. Docking stations 94, 96 and 98 may be operated to selectively warm injection system components within a selected range of temperatures to optimize performance of the lens injection system. Docking stations 94, 96, and 98 may be similarly configured and have similar features as the docking stations 40, 42 and 44, as shown in FIGS. 1-4. For example, the docking station may have a generally cup-like concave configuration, as shown in FIG. 3. Docking stations 94, 96 and 98 may be attached to tray 82 in a similar manner as docking stations 40, 42 and 44 are attached to tray 24.

Docking stations 94, 96 and 98 may include a heating element, for example, heating element 58 shown in FIG. 3, for selectively heating the docking stations. Each docking station may also include a temperature sensor 60 for monitoring a temperature of the docking station.

Surgical cart 84 may include CPU 62, as shown in FIG. 4, for selectively controlling the operation of heating element 58, based at least in part on a signal received from temperature sensor 60. Alternatively, CPU may be integrated into surgical console 88 (see FIG. 6). Surgical cart 84 may include suitable terminals for connecting heating element 58 and temperature sensor 60 to surgical console 88 when the console is mounted on the surgical cart. CPU 62 may be configured and have the same features as described above in connection with surgical console 20.

Docking stations 94, 96 and 98 may also include reader, such as reader 78 (see FIGS. 3 and 4) capable of capturing data stored on identification device 76 (see FIG. 1). Reader 78 may be operably connected to the CPU of console 88 when the console is mounted to surgical cart 84. The reader may operate in substantially the same manner as described above with respect to reader 78. For example, when pack 74 is placed in one of the docking stations, the reader senses the identification device that is incorporated with the pack and proceeds to collect the data stored on identification device. The data may be transmitted to the CPU of surgical console 88, which may use the data to automatically adjust the operating temperature of docking stations 94, 96 and 98 to coincide with the components contained within pack 74.

Referring again to FIG. 1, in addition to, or as an alternative to mounting the docking stations to tray 24, the docking stations may also be formed as an integral part of the surgical console. For example, FIG. 1 illustrates three docking stations 100, 102 and 104, extending from housing 32 of surgical console 20. Integrating the docking stations with the surgical console may be particularly useful in instances where the surgical console and the cart are provided separately, such as shown in FIGS. 5 and 6. Docking stations 100, 102 and 104 may be similarly configured and have similar features as the docking stations 40, 42 and 44, as shown in FIGS. 1-4. For example, each docking station may include a heating element 58 and a temperature sensor 68 for monitoring the temperature of the docking station. The heating elements and temperature sensors may be operably connected to CPU 62, which controls the heat output of the heating elements based, at least in part, on the signals received from the temperature sensors. Docking stations 100, 102 and 104 may also include a reader, such as reader 78 shown in FIGS. 3 and 4, for collecting information regarding items placed in the docking stations.

It will be appreciated that the docking station described herein has broad applications. The foregoing configuration were chosen and described in order to illustrate principles of the methods and apparatuses as well as some practical applications. The preceding description enables others skilled in the art to utilize methods and apparatuses in various configurations and with various modifications as are suited to the particular use contemplated. In accordance with the provisions of the patent statutes, the principles and modes of operation of the disclosed docking station have been explained and illustrated in exemplary configurations.

It is intended that the scope of the present methods and apparatuses be defined by the following claims. However, it must be understood that the disclosed docking station may be practiced otherwise than is specifically explained and illustrated without departing from its spirit or scope. It should be understood by those skilled in the art that various alternatives to the configuration described herein may be employed in practicing the claims without departing from the spirit and scope as defined in the following claims. The scope of the disclosed docking station should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the device and that the method and apparatus within the scope of these claims and their equivalents be covered thereby. In sum, it should be understood that the device is capable of modification and variation and is limited only by the following claims.

What is claimed is:

1. A surgical system comprising:
   a surgical console for performing phacoemulsification including a controller;
   a first docking station having an interior cavity shaped to generally conform to an injection cartridge containing an intraocular lens;
   a second docking station having a second interior cavity shaped to generally conform to a syringe containing a viscoelastic material;
   a first heating element connected to the first docking station and operably connected to the controller;
   a second heating element connected to the second docking station and operably connected to the controller;
   a first temperature sensor attached to the first docking station and operably connected to the controller, the first temperature sensor configured for sending a first signal to the controller indicative of a temperature of the first docking station;
   a second temperature sensor attached to the second docking station and operably connected to the controller, the second temperature sensor configured for sending a second signal to the controller indicative of a temperature of the second docking station;
   a first reader attached to the first docking station and operably connected to the controller, the first reader configured for sending a third signal representative of information collected by the first reader from the injection cartridge placed in the first docking station; and
   a second reader attached to the second docketing station and operably connected to the controller, the second reader configured for sending a fourth signal representative of information collected by the second reader from the viscoelastic placed in the second docking station;
   wherein the controller is configured for selectively adjusting a heat output of the first heating element in response to the first signal and the third signal so as to optimize temperature control of the intraocular lens in the first docking station;
   wherein the controller is configured for selectively adjusting a heat output of the second heating element in response to the second signal and the fourth signal so as to optimize temperature control of the viscoelastic in the second docking station; and
   wherein the controller uses the third signal to verify that the intraocular lens in the first docking station corresponds with an intraocular lens selected for a specific patient.

2. A surgical system comprising:
   a surgical console for performing phacoemulsification including a controller;
   a first docking station having an interior cavity shaped to generally conform to an injection cartridge containing an intraocular lens;
   a second docking station having a second interior cavity shaped to generally conform to a syringe containing a viscoelastic material;
   a first heating element connected to the first docking station and operably connected to the controller;
   a second heating element connected to the docking station and operably connected to the controller;
   a first temperature sensor attached to the first docking station and operably connected to the controller, the first temperature sensor configured for sending a first signal to the controller indicative of a temperature of the first docking station;
   a second temperature sensor attached to the second docking station and operably connected to the controller, the second temperature sensor configured for sending a second signal to the controller indicative of a temperature of the second docking station;
   a first reader attached to the first docking station and operably connected to the controller, the first reader configured for sending a third signal representative of information collected by the first reader from the injection cartridge placed in the first docking station; and
   a second reader attached to the second docking station and operably connected to the controller, the second reader configured for sending a fourth signal representative of information collected by the second reader from the viscoelastic placed in the second docking station;
   wherein the controller is configured for selectively adjusting a heat output of the first heating element in response to the first signal and the third signal so as to optimize temperature control of the intraocular lens in the first docking station;
   wherein the controller is configured for selectively adjusting a heat output of the second heating element in response to the second signal and the fourth signal so as to optimize temperature control of the viscoelastic in the second docking station; and
   wherein the controller uses the third signal and the fourth signal to optimize an intraocular lens-viscoelastic match so as to minimize friction between the intraocular lens and the injection cartridge.

3. A surgical system comprising:
a surgical console for performing phacoemulsification including a controller;
a first docking station having an interior cavity shaped to generally conform to an injection cartridge containing an intraocular lens;
a second docking station having a second interior cavity shaped to generally conform to a syringe containing a viscoelastic material;
a first heating element connected to the first docking station and operably connected to the controller;
a second heating element connected to the docking station and operably connected to the controller;
a first temperature sensor attached to the first docking station and operably connected to the controller, the first temperature sensor configured for sending a first signal to the controller indicative of a temperature of the first docking station;
a second temperature sensor attached to the second docking station and operably connected to the controller, the second temperature sensor configured for sending a second signal to the controller indicative of a temperature of the second docking station;
a first reader attached to the first docking station and operably connected to the controller, the first reader configured for sending a third signal representative of information collected by the first reader from the injection cartridge placed in the first docking station; and
a second reader attached to the second docking station and operably connected to the controller, the second reader configured for sending a fourth signal representative of information collected by the second reader from the viscoelastic placed in the second docking station;
wherein the controller is configured for selectively adjusting a heat output of the first heating element in response to the first signal and the third signal so as to optimize temperature control of the intraocular lens in the first docking station;
wherein the controller is configured for selectively adjusting a heat output of the second heating element in response to the second signal and the fourth signal so as to optimize temperature control of the viscoelastic in the second docking station;
further comprising a third docking station having a third interior cavity shaped to generally conform to an injection handpiece;
wherein the injection handpiece is a powered injection handpiece, and further comprising a third reader attached to the third docking station and operably connected to the controller, the third reader configured for sending a fifth signal representative of information collected by the third reader from the injection handpiece placed in the third docking station; and
wherein the controller uses the third signal and the fifth signal to verify the compatibility of the injection cartridge with the injection handpiece.

* * * * *